(12) United States Patent
Lange et al.

(10) Patent No.: US 6,712,789 B1
(45) Date of Patent: Mar. 30, 2004

(54) INTRODUCER HAVING A MOVABLE VALVE ASSEMBLY WITH REMOVABLE SIDE PORT

(75) Inventors: Michael Lange, White Bear Lake, MN (US); Mark C. Kraus, Independence, MN (US)

(73) Assignee: MedAmicus, Inc., Minneapolis, MN (US)

( * ) Notice: Subject to any disclaimer, the term of this patent is extended or adjusted under 35 U.S.C. 154(b) by 219 days.

(21) Appl. No.: 09/615,276

(22) Filed: Jul. 13, 2000

(51) Int. Cl.$^7$ .............................................. A61M 5/178
(52) U.S. Cl. .................. 604/164.02; 604/160; 604/246; 604/256
(58) Field of Search ................................ 604/160, 161, 604/164.01, 164.02, 164.05, 164.06, 164.07, 247, 244, 256, 246

(56) References Cited

U.S. PATENT DOCUMENTS

| | | | |
|---|---|---|---|
| 4,000,739 A | 1/1977 | Stevens | 128/214.4 |
| 4,345,606 A | 8/1982 | Littleford | 128/784 |
| 4,387,879 A | 6/1983 | Tauschinski | 251/149.1 |
| 4,402,685 A | 9/1983 | Buhler et al. | 604/280 |
| 4,424,833 A | 1/1984 | Spector et al. | 137/849 |
| 4,430,081 A | 2/1984 | Timmermans | 604/256 |
| 4,436,519 A | 3/1984 | O'Neill | 604/175 |
| 4,581,025 A * | 4/1986 | Timmermans | 604/264 |
| 4,610,674 A | 9/1986 | Suzuki et al. | 604/282 |
| 4,626,245 A | 12/1986 | Weinstein | 604/167 |
| 4,723,550 A | 2/1988 | Bales et al. | 128/344 |
| 4,726,374 A | 2/1988 | Bales et al. | 128/344 |
| 4,772,266 A * | 9/1988 | Groshong | 604/164.05 |
| 4,798,594 A | 1/1989 | Hillstead | 604/167 |
| 4,895,565 A | 1/1990 | Hillstead | 604/167 |
| 4,909,798 A | 3/1990 | Fleischhacker et al. | 604/256 |
| 4,929,235 A | 5/1990 | Merry et al. | 604/167 |
| 4,932,633 A | 6/1990 | Johnson et al. | 251/149.1 |
| 4,946,133 A | 8/1990 | Johnson et al. | 251/149.1 |
| 4,997,424 A * | 3/1991 | Little | 604/161 |
| 5,041,095 A | 8/1991 | Littrell | 604/167 |
| 5,092,857 A | 3/1992 | Fleischhacker | 604/256 |
| 5,102,395 A | 4/1992 | Cheer et al. | 604/167 |
| 5,114,408 A | 5/1992 | Fleischhaker et al. | 604/167 |
| 5,125,903 A | 6/1992 | McLaughlin et al. | 604/167 |
| 5,125,904 A | 6/1992 | Lee | 604/164 |
| 5,154,701 A | 10/1992 | Cheer et al. | 604/167 |
| 5,167,637 A | 12/1992 | Okada et al. | 604/167 |
| 5,176,652 A | 1/1993 | Littrell | 604/167 |
| 5,195,980 A | 3/1993 | Catlin | 604/167 |
| 5,267,966 A | 12/1993 | Paul | 604/167 |

(List continued on next page.)

FOREIGN PATENT DOCUMENTS

| | | | |
|---|---|---|---|
| EP | 0544655 | 6/1993 | A61M/39/00 |
| EP | 0593181 | 4/1994 | A61M/5/00 |
| EP | 631793 A1 * | 1/1995 | A61M/25/06 |
| WO | WO-93/20879 | 10/1993 | A61M/25/06 |
| WO | WO-99/34849 | 7/1999 | A61M/5/00 |
| WO | WO-01/32257 | 5/2001 | A61M/39/06 |
| WO | WO 200236179 A2 * | 5/2002 | A61M/00/00 |

*Primary Examiner*—Thomas Denion
*Assistant Examiner*—Ching Chang
(74) *Attorney, Agent, or Firm*—Schwegman, Lundberg, Woessner & Kluth, P.A.

(57) ABSTRACT

An introducing apparatus includes an elongate tubular sheath having an external diameter, and the sheath has a bore including an internal diameter sized to receive a dilator therethrough. The sheath includes at least one tab extending away from a longitudinal axis of the sheath. A movable valve assembly is movably engaged with the tab, where the moving valve is adapted to move from a first position to a second position. In the first position the moving valve is disposed through the longitudinal axis of the sheath. In the second position the moving valve assembly is disposed away from the longitudinal axis of the sheath.

29 Claims, 9 Drawing Sheets

U.S. PATENT DOCUMENTS

| | | | |
|---|---|---|---|
| 5,273,546 A | 12/1993 | McLaughlin et al. | 604/167 |
| 5,304,142 A * | 4/1994 | Liebl et al. | 604/165.02 |
| 5,312,355 A | 5/1994 | Lee | 604/160 |
| 5,350,363 A | 9/1994 | Goode et al. | 604/167 |
| 5,397,311 A | 3/1995 | Walker et al. | 604/160 |
| 5,423,762 A | 6/1995 | Hillstead | 604/167 |
| 5,441,504 A | 8/1995 | Pohndorf et al. | 606/129 |
| 5,520,655 A | 5/1996 | Davila et al. | 604/167 |
| 5,538,505 A | 7/1996 | Weinstein et al. | 604/167 |
| 5,613,953 A | 3/1997 | Pohndorf | 604/165 |
| 5,643,227 A | 7/1997 | Stevens | 604/264 |
| 5,657,963 A * | 8/1997 | Hinchliffe et al. | 251/149.1 |
| 5,755,693 A | 5/1998 | Walker et al. | 604/160 |
| 5,858,007 A | 1/1999 | Fagan et al. | 604/256 |
| 5,897,497 A | 4/1999 | Fernandez | 600/435 |
| 5,906,595 A | 5/1999 | Powell et al. | 604/167 |
| 5,944,697 A | 8/1999 | Biche | 604/174 |
| 6,004,280 A | 12/1999 | Buck et al. | 600/585 |
| 6,024,729 A | 2/2000 | Dehdashtian et al. | 604/256 |
| 6,083,207 A * | 7/2000 | Heck | 604/256 |
| 6,086,570 A | 7/2000 | Aboul-Hosn et al. | 604/256 |
| 6,142,981 A | 11/2000 | Heck et al. | 604/256 |
| 6,322,541 B2 | 11/2001 | West et al. | 604/256 |
| 6,589,262 B1 * | 7/2003 | Honebrink et al. | 606/191 |
| 2001/0049499 A1 | 12/2001 | Lui et al. | 604/164.05 |

* cited by examiner

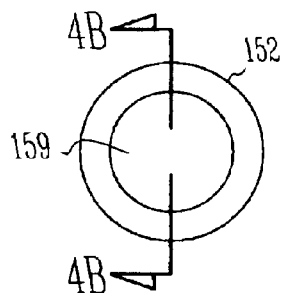
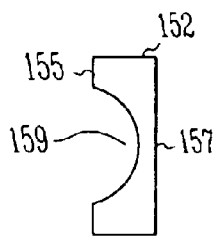
Fig.4A      Fig.4B
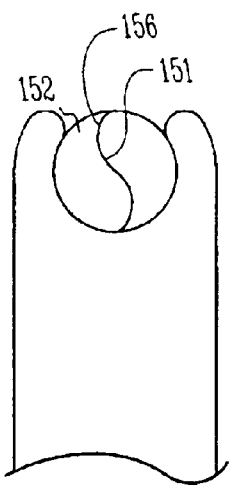
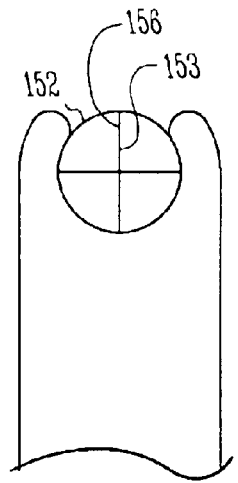
Fig.5A      Fig.5B
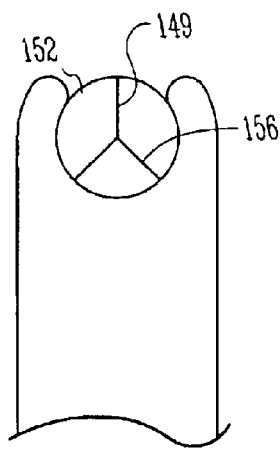
Fig.5C

INTRODUCER HAVING A MOVABLE VALVE ASSEMBLY WITH REMOVABLE SIDE PORT

TECHNICAL FIELD

The present invention generally relates to introducers and introducing assemblies. Specifically, it relates to an introducer with a hemostatic valve.

BACKGROUND

Introducer devices are employed for inserting catheters, guidewires, or other medical devices into patients. A typical procedure provides for insertion of a needle into the vasculature of a patient. After insertion of the needle, a guide wire is inserted through the needle, and the needle is removed. The dilator and the sheath are inserted over the guidewire, and the dilator and guidewire may be removed leaving the sheath protruding from the patient's vein. A diagnostic or therapeutic catheter (e.g. a central venous access catheter) or guide wire or other medical device, is then inserted through the sheath into the patient.

Peelable sheaths are available, where the sheath can be peeled off of a catheter, for example, as that shown in U.S. Pat. No. 4,345,606 to Littleford on Aug. 24, 1982. However, once a sheath is inserted, and the dilator and guidewire have been removed, the sheath provides a passage for a flow of blood, where such uncontrolled blood loss can have a negative affect on a patient. Another problem with the sheath is that the sheath allows for the introduction of air into the vein of the patient. If air is inadvertently introduced into the vein, an air embolism may result with negative effects. One solution is found in U.S. Pat. No. 5,304,142 issued to Liebl on Apr. 19, 1994, and assigned to Medamicus, Inc. Another approach is described in U.S. Pat. No. 5,125,904, issued to Lee in Jun. 30, 1992. However, the sheath in the '904 Patent may experience resistance to pulling apart, and separating the sheath may prove to be difficult. In addition, the technician may experience difficulty in inserting an instrument or medical device through the valve. One solution is to lubricate the valve with silicone. However this results in silicone becoming inadvertently transferred to other medical instruments, or technicians.

Accordingly, what is needed is an introducer and dilator which seals an introducer to a catheter or other medical instruments. What is also needed is a sealing device which does not distract or interfere with the implantation process.

SUMMARY

An introducing apparatus includes an elongate tubular sheath having an external diameter, and the sheath has a bore including an internal diameter sized to receive a dilator therethrough, where the sheath is separable. The sheath includes at least one tab extending away from a longitudinal axis of the sheath. A sliding valve assembly is slidingly engaged with the tab, where the sliding valve is adapted to slide from a first position to a second position. In the first position the sliding valve is disposed through the longitudinal axis of the sheath. In the second position the sliding valve assembly is disposed away from the longitudinal axis of the sheath.

Options for the above introducing apparatus include as follows. In one option, the sliding valve assembly includes a membrane coupled with a sliding member, where the membrane optionally includes a slit therein. Alternatively, the tab is defined in part by a tab longitudinal axis, and the sliding valve assembly is adapted to slide along the tab longitudinal axis. In another option, the sliding valve assembly is adapted to rotate about a hinge point on the at least one tab. Optionally, the introducing apparatus includes a removable side port. In yet another option, the sliding valve assembly includes a valve support member coupled with a seal, and the valve support member extends only partially around the seal.

An introducing apparatus includes an elongate tubular sheath having an external diameter, and the sheath has a bore including an internal diameter sized to receive a dilator therethrough. The sheath includes at least one tab extending away from a longitudinal axis of the sheath. A movable valve assembly is movably engaged with the tab, where the movable valve is adapted to move from a first position to a second position. In the first position the movable valve is disposed through the longitudinal axis of the sheath. In the second position the movable valve assembly is disposed away from the longitudinal axis of the sheath.

Options for the above introducing apparatus include as follows. One example of an option is that the movable valve assembly is adapted to slide relative to the tab. In another example of an option, the sheath is optionally separable. In another option, the sliding valve assembly includes a membrane coupled with a moving member, where the membrane optionally includes a slit therein. Alternatively, the tab is defined in part by a tab longitudinal axis, and the movable valve assembly is adapted to slide along the tab longitudinal axis. In another option, the movable valve assembly is adapted to rotate about a hinge point on the at least one tab. Optionally, the introducing apparatus includes a removable side port. In yet another option, the movable valve assembly includes a valve support member coupled with a seal, and the valve support member extends only partially around the seal.

A method includes inserting an introducing apparatus into a body. The introducing apparatus includes an elongate tubular sheath which has an external diameter, and the sheath has a bore including an internal diameter sized to receive a dilator therethrough. The sheath includes at least one tab which extends away from a longitudinal axis of the sheath. A movable valve assembly is movably coupled with the at least one tab. The method further includes moving the valve assembly from a first position to a second position. In the first position, the movable valve assembly is disposed through the longitudinal axis of the sheath. In the second position the movable valve assembly is disposed away from the longitudinal axis of the sheath. Optionally, the method further includes flexing the valve assembly as an instrument is inserted therethrough.

An introducing apparatus is also described which includes an elongate, separable tubular sheath that is defined in part by an external diameter. The sheath includes a bore which has an internal diameter sized to receive a dilator therethrough. The sheath further includes at least one tab that extends away from a longitudinal axis of the sheath. The introducing apparatus further includes a side port assembly removably coupled with the sheath. The side port assembly is adapted to be removed from the sheath without damage or separation of the sheath. In one option, the side port assembly is coupled with the sheath with a snap-fit connection. Alternatively, the side port assembly is threadingly coupled with the sheath. In another option, the side port assembly includes a valve disposed between the sheath and the side port.

The present introducing assembly requires fewer parts, and is cheaper to make. In addition, since the valve is optionally moved away from the longitudinal axis prior to splitting of the sheath, the splitting of the sheath is easier to do. The implanter has more options in sealing the introducing apparatus, including the option of having the valve moved out of the way during a procedure. A further benefit is that a more effective seal is made around the catheter or medical instrument since the device which retains or supports the valve optionally flexes, for example, as instruments are inserted therethrough. Furthermore, the introducing assembly allows for more flexible instruments to be inserted therethrough, where no damage occurs to the distal end of the flexible instruments which might occur with prior valve designs.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 4A illustrates a top plan view of a portion of an introducing apparatus as constructed in accordance with one embodiment.

FIG. 4B illustrates a cross-sectional view taken along 4A—4A on FIG. 4A.

FIG. 5A illustrates a top plan view of a portion of an introducing apparatus as constructed in accordance with one embodiment.

FIG. 5B illustrates a top plan view of a portion of an introducing apparatus as constructed in accordance with one embodiment.

FIG. 5C illustrates a top plan view of a portion of an introducing apparatus as constructed in accordance with one embodiment.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
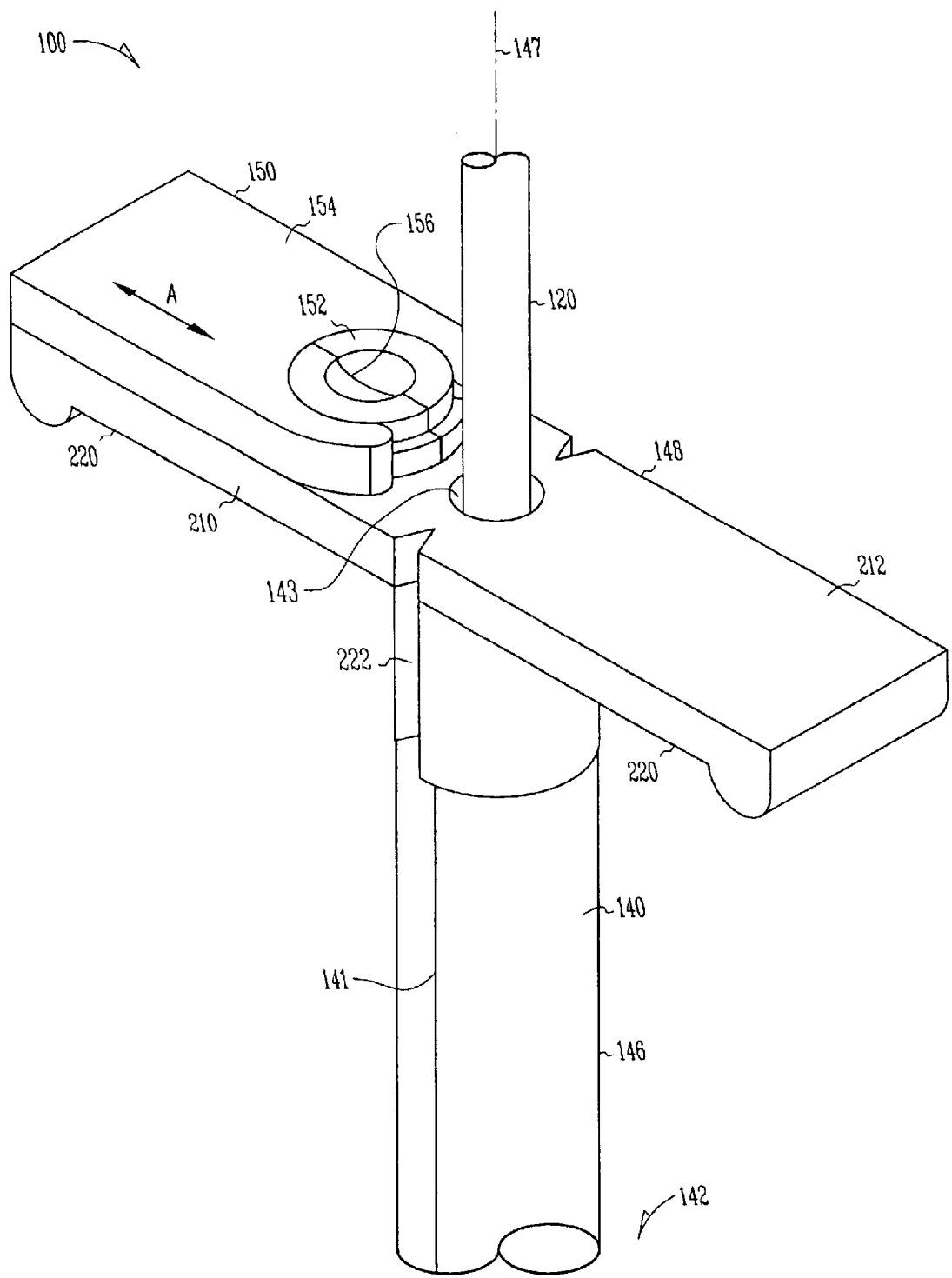
FIG. 1A illustrates a perspective view of an introducing apparatus as constructed in accordance with one embodiment.

An introducer assembly 100, as shown in FIG. 1A, includes generally a sheath 140 and a dilator 120. The dilator 120 allows for the introducer assembly 100 to be introduced into a vein of a patient, for instance, over a guidewire. The dilator 120 extends from a distal end to a proximal end, where the distal end is insertable into a patient. The distal end optionally ends in a tapered end. At the proximal end is a hub having a bore therethrough. The dilator 120 also includes a passage therethrough, aligned with the bore, which allows the dilator 120 to be inserted over a guidewire or a catheter. The dilator 120 is sized to be received by the sheath 140 therein.

The sheath 140 allows for additional instruments to be inserted therethrough and inserted into the patient. The sheath 140 includes various types of sheaths, for instance, the sheath 140 can comprise a sheath which has a strengthening braid of material. Alternatively, the sheath 140 includes those which are modified to prevent bends in the elongate sheath. The sheath 140 is defined in part by a longitudinal axis 147, and the sheath 140 extends from a distal end 142 to a proximal end 148. The distal end 142 is first inserted into the patient and the proximal end 148 remains outside of the patient. Near the distal end 142 is a tapered portion which provides a transition to a cylindrical portion 146. The sheath 140 also includes a passage 143 therethrough, where the passage 143 is substantially aligned with the longitudinal axis 147 of the sheath 140. The passage 143 allows for the introduction of the dilator 120 therethrough. After the introducer assembly 100 has been inserted into a patient, and the dilator 120 is removed, other medical instruments can be easily inserted into and through the sheath 140, and introduced into the patient.

The sheath 140 includes at least one tab 210 which extends radially outward from the sheath 140. In one embodiment, the sheath 140 includes two tabs 220 which are disposed 180 degrees from each other. Optionally, tab break lines 222 are disposed between along the sheath 140, for instance between the two tabs 220

In another option, the sheath 140 is splittable such that the sheath 140 is separable into two or more components. The sheath 140 is separable, splittable, or slittable which prevents disruption to or removal of instruments or devices which have been inserted through the sheath 140. The separable sheath 140 is splittable in a number of manners such as including at least one score line 141. The sheath 140 is scored, and optionally two scores 141 are approximately 180 degrees from each other. The scores 141 are aligned with the optional tab break lines 222 such that the tab break lines 222 and the scores 141 are disposed between the two tabs 220. Alternatively, the sheath 140 is separable using a slitting device, a rip cord or strengthening strip running along the longitudinal length of the sheath, a weakening which allows the introducer to be ripped apart, or other techniques which allow the sheath 140 to separate into two or more components.

A valve assembly 150 is coupled with the at least one tab 210 of the sheath. Optionally, the valve assembly 150 is movably coupled with the at least one tab 210, where the valve assembly 150 is movable relative to a top surface 212 of the at least one tab 210. In another example, the valve assembly 150 is slidingly coupled with the at least one tab 210, as further described below.

The valve assembly 150 includes a seal 152 and a valve support member 154. The valve support member 154, in combination with the seal 152, provide a hemostatic valve which seals against instruments which are disposed therethrough. In addition, the valve assembly 150 provides a seal for the passage 143 of the sheath 140, where little or no air is allowed to enter the vein of a patient. The valve support member 154 comprises a single component which extends only partially around the seal 152, and is adapted to retain the seal 152 within an opening 149 of the valve support member 154. Since the valve support member 154 extends only partially around the seal 152, the valve assembly 150 is easily moved to and away from the longitudinal axis 147 of the sheath, regardless if an instrument is present therein. With respect to the seal 152, suitable materials include, but are not limited to, silicone, polyurethane, or rubber. The seal 152, in one option, comprises a single membrane. In one alternative, the seal 152 comprises two or more portions of a membrane which are held in place by the valve support member 154.

FIGS. 4A and 4B illustrate an alternative for the seal 152. The seal 152 is defined in part by a top surface 155 and a bottom surface 157. The seal 152 further includes a generally central recessed portion 159, where the recessed portion 159 is recessed away from the top surface 155. Optionally, the recessed portion 159 can be recessed away from the bottom surface 157 and/or recessed away from the top surface 155. The recessed portion 159, which alternatively can be offset from a central region, is the portion of the seal 152 which is directly adjacent to, or is where an instrument is disposed therethrough. The recessed portion 159 allows for lesser material to be provided for the seal 152 without affecting the pressure of the seal relative to the sheath and/or the instrument. This allows for an increased variety of instruments to be successfully disposed therethrough, without, for instance, damage to a softer instrument, or without damage to a distal tip of the instrument. Furthermore, the lack of damage to the instrument allows for the physician to implant the instrument within a patient without distraction to the physician from concern of risk or actual damage to the instruments.

A further option is that the seal 152 includes a slitted portion 156 therein, as shown in FIGS. 1A, 1B, 5A, and 5B. The slitted portion 156 can include, but is not limited to, a number of different options such as a slit, a partial slit, a line of weakness, a perforated line, or a complete cut through the seal 152. Alternatively, the slitted portion 156 extends only partially from one side surface to another, as shown in FIG. 4A. In yet another option, the seal 152 comprises multiple sealing components, for instance, which are disposed adjacent to one another. FIGS. 5A, 5B, and 5C illustrate alternative configurations for the seal 152. As shown in FIG. 5A, the seal 152 includes a cut 151 which has a wave-shape. Advantageously, the wave-shape assists in preventing the valve assembly from inadvertently sliding off of an instrument disposed therethrough. In another alternative, as shown in FIG. 5B, the seal 152 includes a cross cut 153, which further aids in the movement of the movable valve assembly around instruments disposed therethrough. In a further alternative, as shown in FIG. 5C, the seal 152 includes a Y-shaped cut 149. The Y-shaped cut 149, the wave shape cut 151, and/or the cross cut 153 optionally extend only partially from one side surface to another. It should be noted that other variations to the slit are possible, and are considered within the scope of the invention.

The valve support member 154 retains the seal 152 thereto, as further described below. In addition, the valve support member 154 is coupled with the sheath 140, and allows for the valve assembly 150 to move relative to the sheath 140. The valve support member 154 is coupled with the seal 152 and the sheath 140 in a variety of different manners. For instance, the valve support member 154 is optionally removably coupled with the sheath 140, for example, with a snap-fit connection. Alternatively, the valve support member 154 is removably coupled with the sheath 140 by adhesively bonding the valve support member 154 with the sheath 140. Another option includes insert molding the valve support member 154 with the sheath 140. Removably coupling the valve support member 154 allows for further options for the physician during the implant process, and also allows for the introducing apparatus to be fabricated in a more cost efficient manner.

Figure 2C:
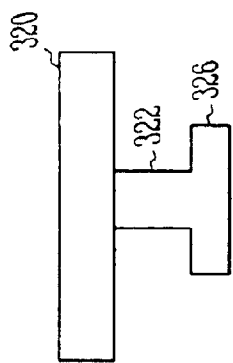
FIG. 2C illustrates a second side elevational view of a portion of an introducing apparatus as constructed in accordance with one embodiment.
Figure 2A:
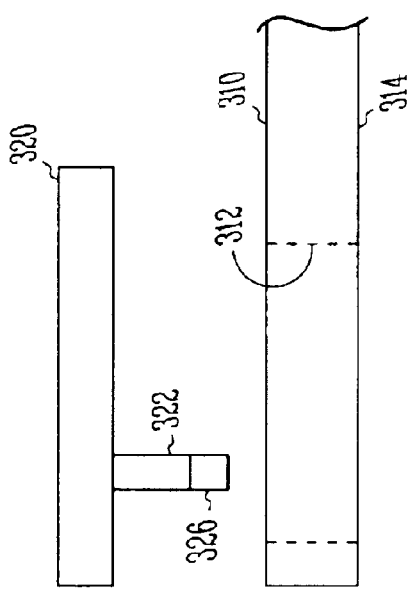
FIG. 2A illustrates a first side elevational view of a portion of an introducing apparatus as constructed in accordance with one embodiment.
Figure 2B:
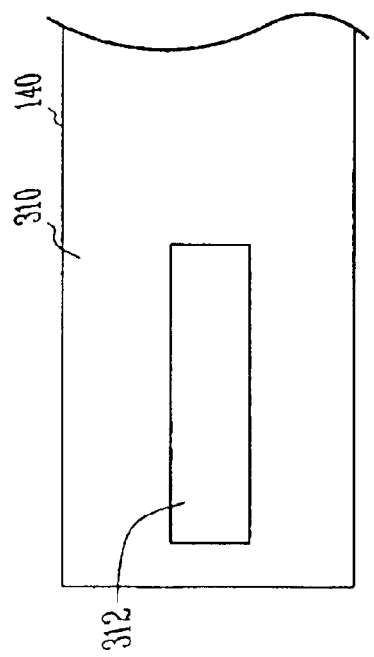
FIG. 2B illustrates a top plan view of a portion of an introducing apparatus as constructed in accordance with one embodiment.

In another option, as shown in FIGS. 2A, 2B, and 2C, the tab 310 of the sheath 140 includes a cut out 312 therein. The cut out 312 is sized and positioned to receive therein a portion of the valve support member 320. The valve support member 320 includes a member 322 extending therefrom. The member 322 is disposed through the cut out 312, such that the member 322 is movably disposed within the cut out 312. As the member 322 moves within the cut out 312, the valve support member 320 moves relative to the tab 310 of the sheath 140. Coupled with the member 322 is a flange 326 which extends from the member 322. The flange 326 extends under a surface 314 of the tab 310, which retains the valve support member 320 to the tab 310.

Figure 3:
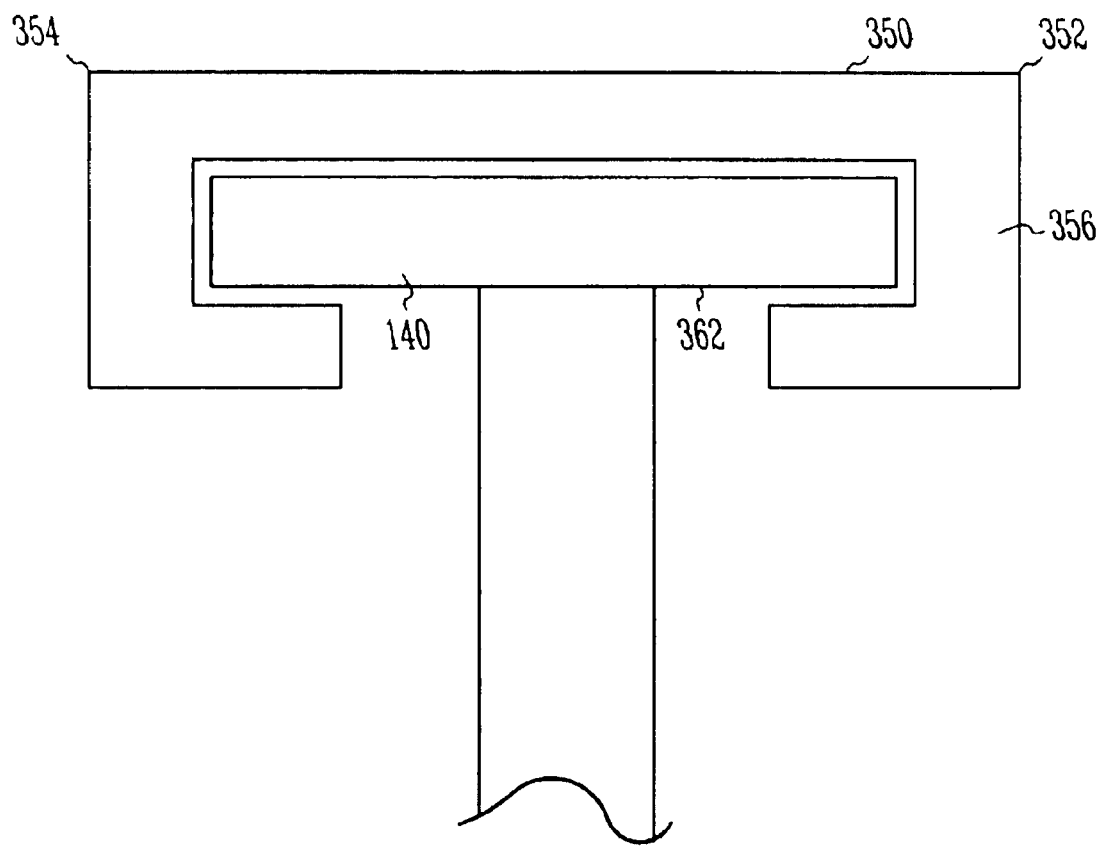
FIG. 3 illustrates a side elevational view of a portion of an introducing apparatus as constructed in accordance with another embodiment.

FIG. 3 illustrates another alternative manner in which the valve assembly 150 is movably coupled with the sheath 140. The valve assembly 150 includes a valve support member 350 which extends from a first side 352 to a second side 354. Coupled with the first side 352 and/or the second side 354 is an arm 356. The arm 356 is generally L-shaped and wraps around at least a portion of the tab 362 of the sheath 140. The arm 356 is sized and positioned to movably couple the valve assembly 150 with the sheath 140. Optionally, the arm 356 allows for the valve assembly 150 to be removably coupled with the sheath 140.

Figure 1B:
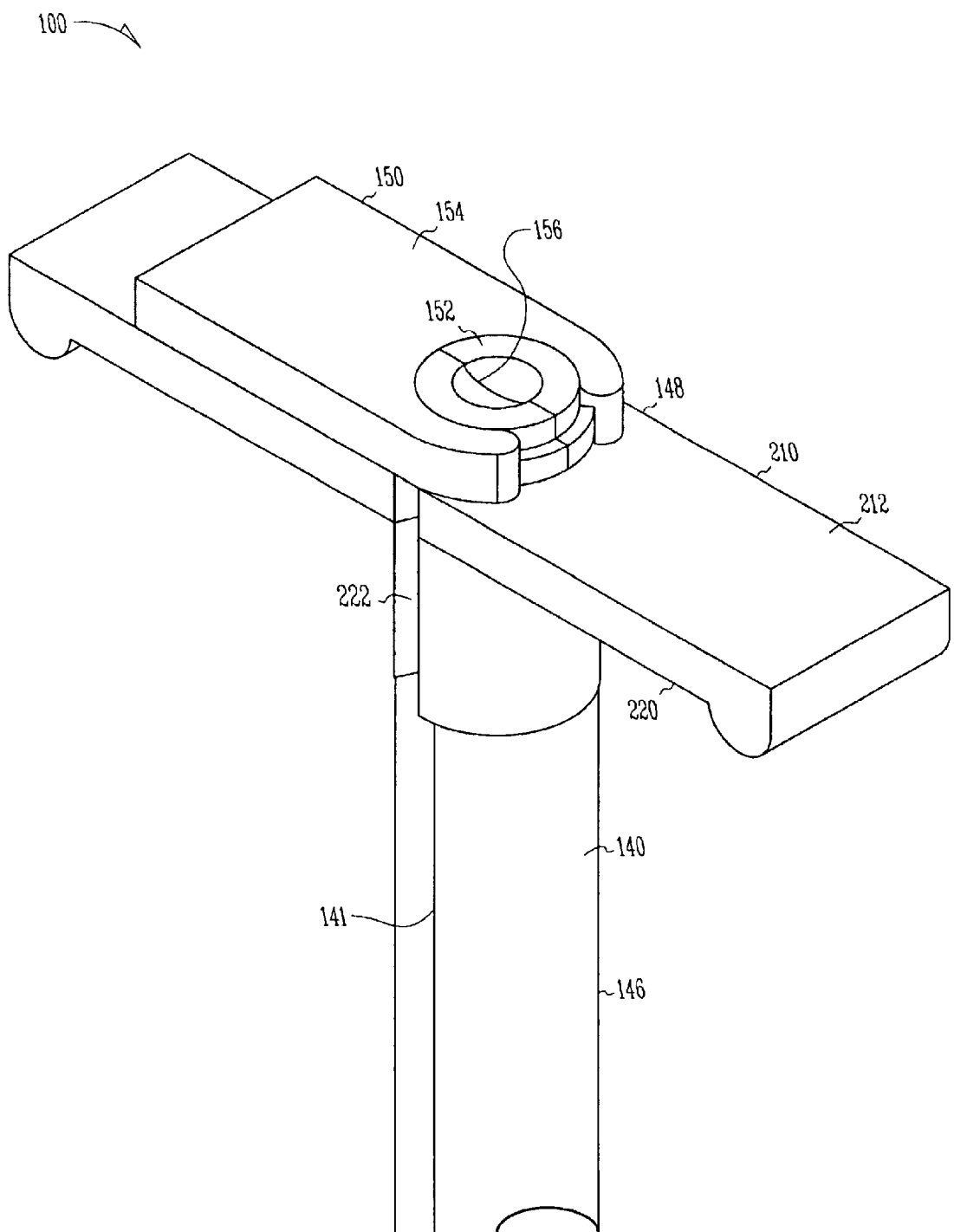
FIG. 1B illustrates a perspective view of an introducing apparatus as constructed in accordance with one embodiment.

The valve assembly 150 moves relative to the sheath in many different manners. In one example, as shown in FIGS. 1A and 1B, the valve support member 154 is adapted to slide along a longitudinal axis of the at least one tab, along "A". The valve support member 154, in one option, is disposed around only a portion of the seal 152. In another option, the valve support member 154 flexes as an instrument is disposed through the seal 152. The movable valve assembly 150 is adapted to slide from a first position, as shown in FIG. 1B, to a second position, as shown in FIG. 1A. In the first position, the movable valve assembly 150 is disposed through the longitudinal axis of the sheath, sealing the passage of the sheath 140. In the second position, the movable valve assembly 150 is disposed away from the longitudinal axis of the sheath.

Figure 6:
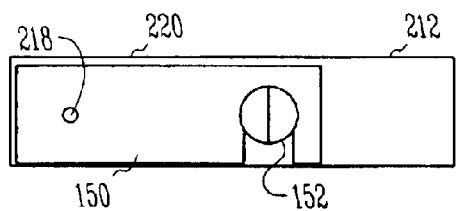
FIG. 6 illustrates a side elevational view of an introducing apparatus as constructed in accordance with one embodiment.
Figure 7:
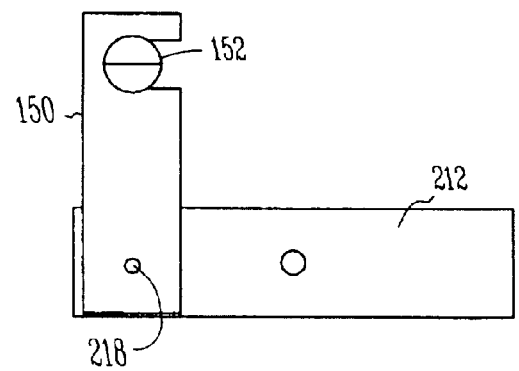
FIG. 7 illustrates a side elevational view of an introducing apparatus as constructed in accordance with one embodiment.
Figure 8:
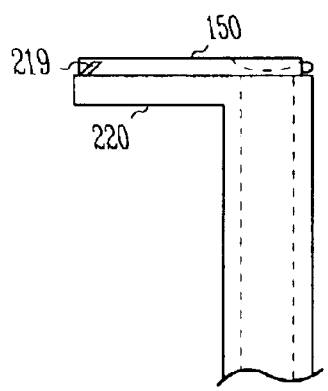
FIG. 8 illustrates a side elevational view of an introducing apparatus as constructed in accordance with one embodiment.
Figure 9:
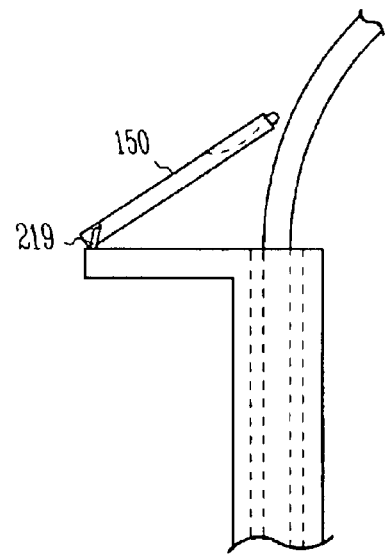
FIG. 9 illustrates a side elevational view of an introducing apparatus as constructed in accordance with one embodiment.

In another example, as shown in FIGS. 6 and 7, the movable valve assembly 150 is adapted to rotate about a hinge point 218 on the at least one tab of the sheath. As the movable valve assembly 150 rotates, the valve assembly 150 slides on a top surface 212 of the at least one tab 220. In another embodiment, as shown in FIGS. 8 and 9, the movable valve assembly 150 is adapted to rotate about a hinge point 219 on the at least one tab 220. As the movable valve assembly 150 rotates about the hinge point, at least a portion of the valve assembly 150 is lifted away from the top surface of the at least one tab. In yet another option, the introducer apparatus includes a removable side port, as shown in FIGS. 10–12.

Figure 10:
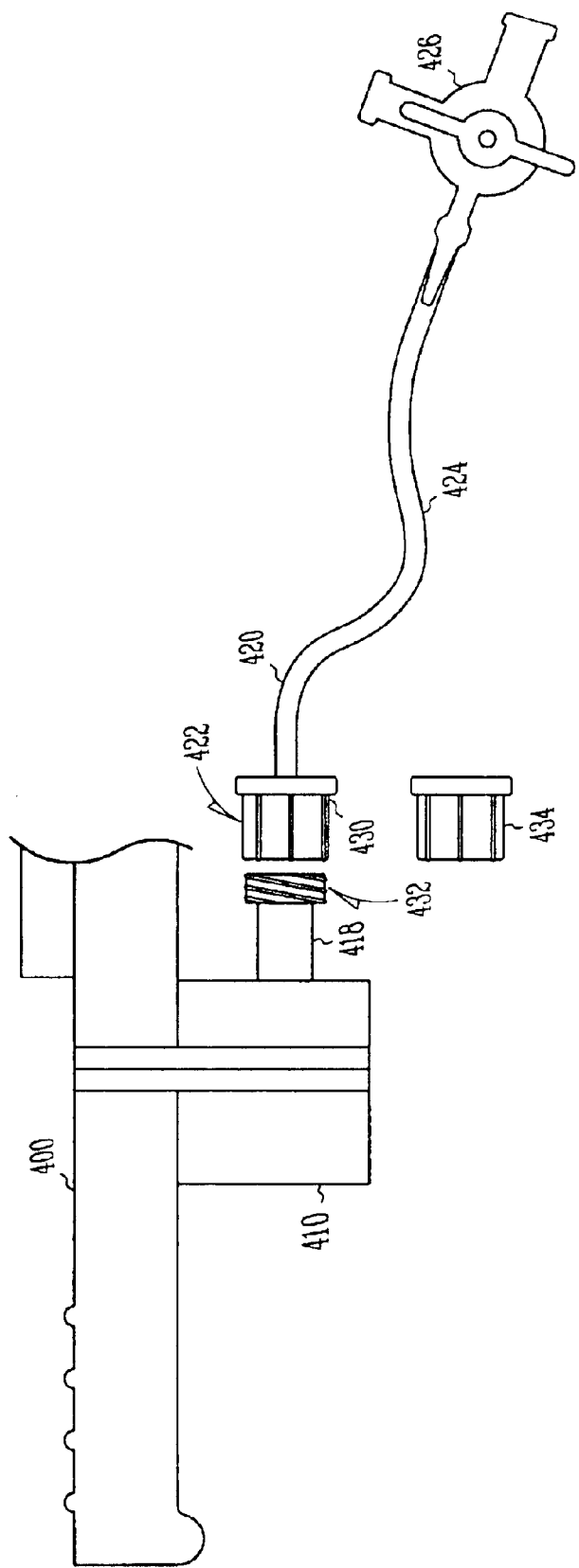
FIG. 10 illustrates a side view of a portion of an introducing apparatus as constructed in accordance with another embodiment.

A portion of an introducer apparatus 400 is shown in FIG. 10 which includes a removable side port 420. The introducer apparatus 400, which is illustrated in FIGS. 10–12, optionally includes the movable valve assembly as discussed for the various embodiments described above. The removable side port 420 allows for the introduction of fluids such as saline or medicine through the sheath 410 without having to remove instruments disposed through the sheath 410. The removable side port 420 includes a coupling member 422 adapted to couple with a member 418 on the introducer apparatus 400, where the member 418 is disposed, in one option, on the sheath 410. Tubing 424 is connected between the coupling member 422 and a stopcock assembly 426, which facilitates the introduction of fluids therein.

The removable side port 420 is removably coupled with the sheath 410 in a number of manners. For instance, the coupling member 422 includes a threaded rotating collar 430 which is adapted to be threadingly coupled with a threaded portion 432 of the member 418. Optionally, when the coupling member 422 is removed from the member 418, a cap 434 is disposed thereon to prevent blood loss and/or the introduction of air into the patient.

Figure 11:
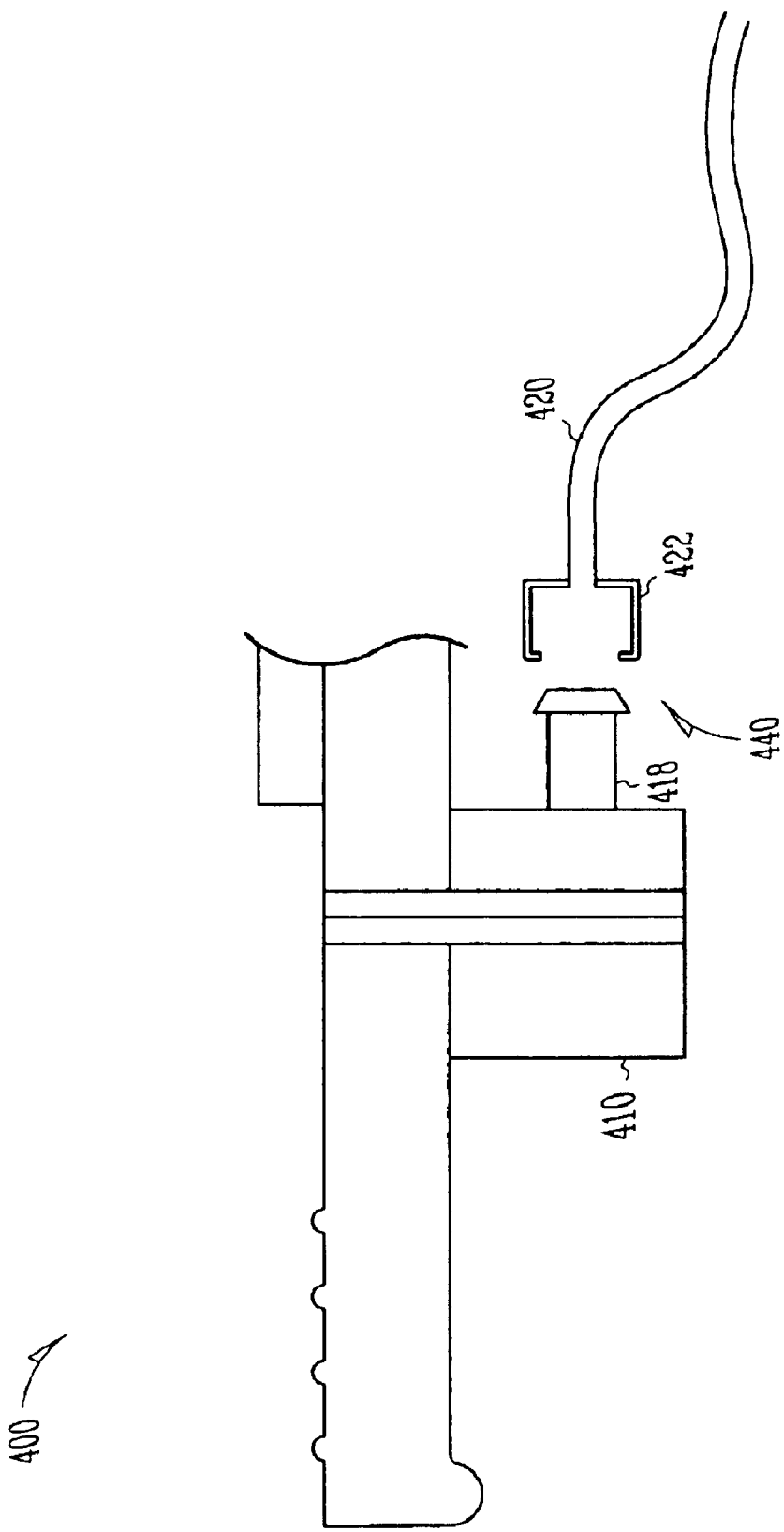
FIG. 11 illustrates a side view of a portion of an introducing apparatus as constructed in accordance with another embodiment.
Figure 12:
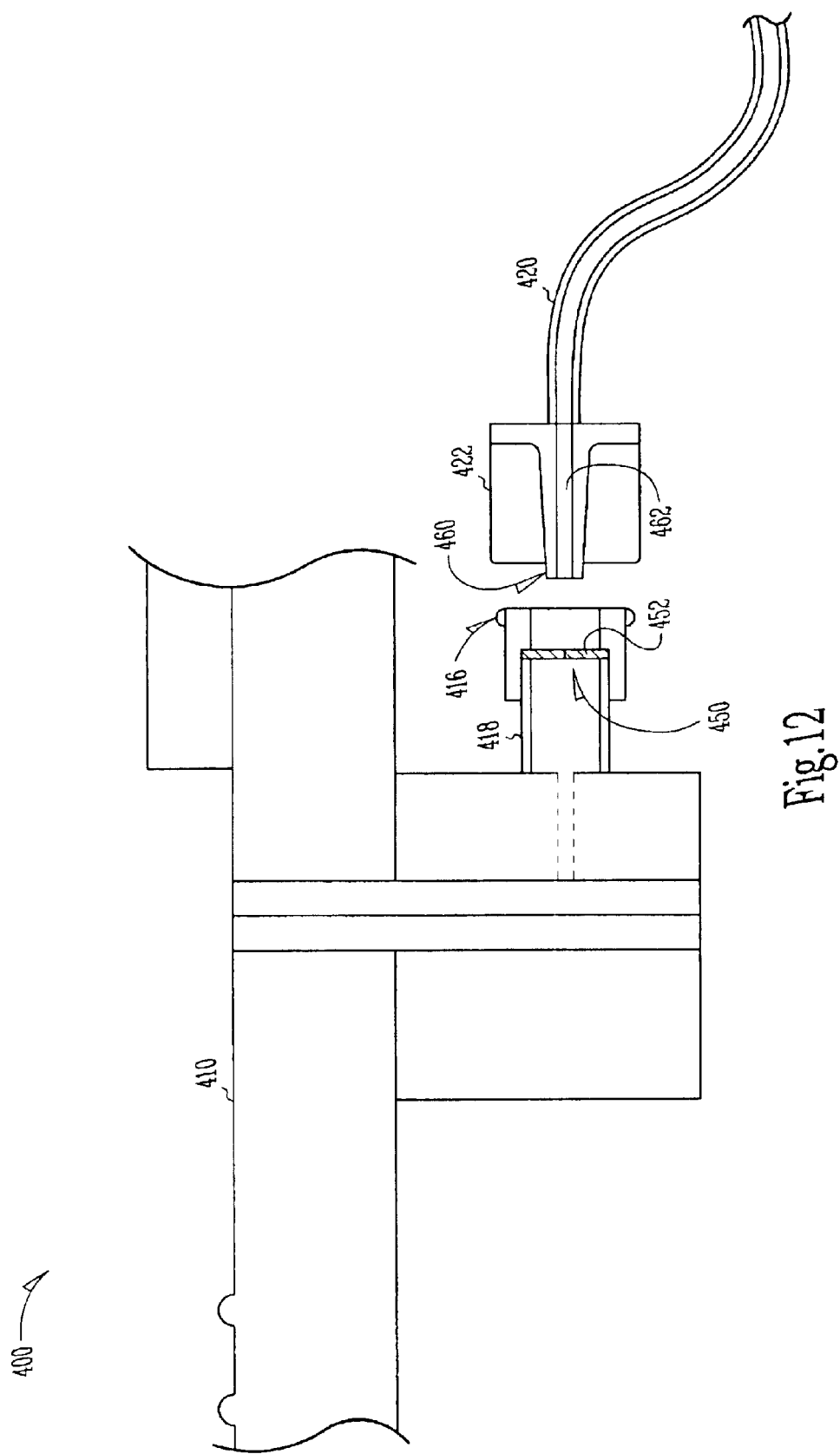
FIG. 12 illustrates a side view of a portion of an introducing apparatus as constructed in accordance with another embodiment.

FIG. 11 illustrates another embodiment of an introducer apparatus 400 having a removable side port 420. The removable side port 420 includes a coupling member 422 which is adapted to be removably coupled with the member 418. The member 418 and the coupling member 422 include snap-fit features 440 which allow for the member 418 and the coupling member 422 to be snap-fitted together. In one option, the member 418 includes a flange 442 which is received by the coupling member 422. Alternatively, the coupling member 422 is sized and positioned to fit with the member 418 by an interference fit.

FIG. 12 illustrates yet another option of an introducer apparatus 400 having a removable side port 420. The removable side port 420 includes a coupling member 422 which is adapted to be removably coupled with the member 418. The member 418 includes features which allow for the member 418 be coupled with the removable side port 420. For instance, the member 418 includes a luer thread 416. In addition, the member 418 includes a valve 450 which prevents blood loss and air embolism when the removable side port 420 is detached. The valve 450 is disposed between the sheath 410 and the removable side port 420, and optionally comprises a silicone membrane 452.

The coupling member 422 includes an component 460 which is adapted to open the valve 450 when the coupling member 422 is coupled with the member 418. The component 460 includes a passage 462 therethrough which permits the introduction of fluids and/or medicine through the removable side port 420. Advantageously, when the coupling member 422 is removed from the sheath 410, the valve 450 seals the sheath 410, thereby preventing blood loss and air embolism.

Use of the apparatus, as described above and including the many variations, includes inserting an introducing apparatus into a body of a patient. For instance, the introducing apparatus includes an elongate tubular sheath which has an external diameter, and the sheath has a bore including an internal diameter sized to receive a dilator therethrough. The sheath includes at least one tab extends away from a longitudinal axis of the sheath. A movable valve assembly is movably coupled with the at least one tab. The valve assembly is moved from a first position to a second position. In the first position, the movable valve assembly is disposed through the longitudinal axis of the sheath. In the second position the movable valve assembly is disposed away from the longitudinal axis of the sheath. Optionally, the method further includes flexing the valve assembly as an instrument is inserted therethrough.

The present introducing assembly requires fewer parts, and is cheaper to make. In addition, since the valve is optionally removed prior to splitting of the sheath, the splitting of the sheath is easier to do. Furthermore, since the two or more membrane portions, or a slitted member, are already separated from one another as the seal is moved around and away from an instrument, each of use of the device is increased since the seal and the valve support member need not be peeled away from the instrument. Further, since the valve apparatus can be moved away from the longitudinal axis of the sheath prior to insertion of an instrument therethrough, smaller and/or more flexible instruments can be used with the introducing assembly. Still further, the optional recessed portion of the seal allows for less resistance as an instrument is inserted therethrough.

The implanter has more options in sealing the introducing apparatus, including the option of having the valve moved out of the way during a procedure. A further benefit is that a more effective seal is made around the catheter or medical instrument since the device which retains or supports the valve optionally flexes, for example, as instruments are inserted therethrough.

It is to be understood that the above description is intended to be illustrative, and not restrictive. Many other embodiments will be apparent to those of skill in the art upon reading and understanding the above description. It should be noted that embodiments or portions thereof discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. An introducing apparatus comprising:
   an elongate tubular sheath having an external diameter, the sheath having a bore including an internal diameter sized to receive a dilator therethrough, where the sheath is separable;
   the sheath extending from a distal end to a proximal end;
   the sheath including at least one tab extending away from a longitudinal axis of the sheath, the at least one tab including a tab, the tab having a tab longitudinal axis;

a sliding valve assembly slidingly engaged with the tab along the tab longitudinal axis, the sliding valve assembly including a membrane; and the sliding valve adapted to slide from a first position to a second position relative to the tab while an instrument is inserted through the bore and through the membrane, in the first position the sliding valve and the membrane disposed through the longitudinal axis of the sheath, in the second position the sliding valve and the membrane disposed away from the longitudinal axis of the sheath.

2. The introducing apparatus as recited in claim 1, wherein the sliding valve assembly includes a sliding member disposed around at least more than half of an outer perimeter of the membrane.

3. The introducing apparatus as recited in claim 2, wherein the membrane includes two or more membrane components.

4. The introducing apparatus as recited in claim 2, wherein the membrane includes at least one slit therin.

5. The introducing apparatus as recited in claim 4, wherein the at least one slit has a wave shape.

6. The introducing apparatus as recited in claim 4, wherein the at least one slit has a cross-shape or a Y-shape.

7. The introducing apparatus as recited in claim 1, wherein the sliding valve assembly is adapted to rotate about a hinge point on the at least one tab.

8. The introducing apparatus as recited in claim 1, further comprising a removable side port.

9. The introducing apparatus as recited in claim 1, wherein the sliding valve assembly includes a valve support member extending only partially around the membrane.

10. The introducing apparatus as recited in claim 1, wherein the sliding valve assembly includes a valve support member coupled with a seal, and the valve support member includes at least one arm encompassing the tab.

11. The introducing apparatus as recited in claim 1, wherein the sliding valve assembly includes a valve support membrane coupled with a seal, the at least one tab including a recess therein, the valve support member includes a member extending therefrom, the member sliding disposed within the recess.

12. The introducing apparatus comprising:

an elongate tubular sheath having an external diameter, the sheath having a bore including an internal diameter sized to receive a dilator therethrough;

the sheath extending from a distal end to a proximal end, the sheath comprising a separable sheath;

the sheath at least one tab including a tab extending away from a longitudinal axis of the sheath;

a moveable valve assembly including a membrane movably coupled relative to the tab, the moveable valve assembly movable from a second position to a first position while an instrument is disposed therethrough, in the first position the membrane of the movable valve assembly is disposed through the longitudinal axis of sheath, in the second position the membrane of the movable valve assembly disposed away from the longitudinal axis of the sheath.

13. The introducing apparatus as recited in claim 12, wherein the tab is defined in part by a tab longitudinal axis, and the sliding valve assembly is adapted to slide along the tab longitudinal axis.

14. An introducing apparatus as recited in claim 12, wherein the movable valve assembly is adapted to slide relative to the tab.

15. The introducing apparatus as recited in claim 13, wherein the membrane has a recess that is recessed away from a top surface of the membrane.

16. The introducing apparatus as recited in claim 15, wherein the membrane includes a slit therein.

17. The introducing apparatus as recited in claim 12, wherein the tab is defined in part by a tab longitudinal axis, and the movable valve assembly is slidable along the tab longitudinal axis.

18. The introducing apparatus as recited in claim 12, wherein the movable valve assembly is adapted about a hinge point on the at least one tab.

19. The introducing apparatus as recited in claim 12, further comprising a removable side port.

20. The introducing apparatus as recited in claim 12, wherein the sliding valve assembly includes a valve support member extending only partially around the membrane.

21. An introducing apparatus comprising:

an elongate tubular sheath having an external diameter, the sheath having a bore including an internal diameter sized to receive a dilator therethrough, the sheath comprising a separable sheath;

the sheath extending from a distal end to a proximal end;

the sheath including at least one tab including a tab extending away from a longitudinal axis of the sheath;

a valve assembly coupled with the tab, the valve assembly including a sealing membrane having a slit therein; and a means for moving the valve assembly relative to the at least one tab while an instrument is inserted through the bore and through the membrane.

22. The introducing apparatus as recited in claim 21, further comprising a removable side port coupled with the sheath.

23. A method comprising:

inserting an introducing apparatus into a body, the introducing apparatus including an elongate tubular sheath having an external diameter, the sheath having a bore including an internal diameter sized to receive a dilator therethrough;

the sheath extending from a distal end to a proximal end;

the sheath including at least one tab including a tab extending away from a longitudinal axis of the sheath;

a movable valve assembly movably coupled relative to the tab, the movable valve assembly including a membrane having a line of weakness, the movable valve assembly adapted to seal a longitudinal passage of the sheath; and inserting an instrument through the membrane; and moving the valve assembly from a first position to a second positon while the instrument is disposed through the membrane, in the first position the movable valve assembly disposed through the longitudinal axis of the sheath, in the second position the movable valve assembly disposed away from the longitudinal axis of the sheath.

24. The method as recited in claim 23, further comprising moving the valve aseembly from the second position to the first position prior to separating the sheath.

25. The method as recited in claim 23, further comprising removing a removalbe side port coupled with the sheath.

26. An introducing apparatus comprising:

an elongate tubular sheath having an external diameter, the sheath having a bore including an internal diameter sized to receive a dilator therethrough, where the sheath is separable;

the sheath extending from a distal end to a proximal end;

the sheath including at least one tab including a tab extending away from a longitudinal axis of the sheath; and a valve assembly movably coupled relative to the tab, the valve assembly including a membrane, the valve assembly extending only partially around a perimeter of the membrane, the membrane disposed over the bore in a first position, the valve assembly movable from the first position to a second position away from the bore while an instrument is inserted through the bore and the membrane.

27. The introducing apparatus as recited in claim 26, wherein the membrane includes a hemispherical recess therein.

28. The introducing apparatus as recited in claim 26, wherein the membrane is disposed on a top surface of the tab.

29. The introducing apparatus as recited in claim 26, wherein the valve assembly is slidable relative to a tab longitudinal axis.

* * * * *

UNITED STATES PATENT AND TRADEMARK OFFICE
CERTIFICATE OF CORRECTION

PATENT NO. : 6,712,789 B1
DATED : March 30, 2004
INVENTOR(S) : Lange et al.

Page 1 of 1

It is certified that error appears in the above-identified patent and that said Letters Patent is hereby corrected as shown below:

Title page, Item [54] and Column 1, lines 1-2,
Title, delete "INTRODUCER HAVING MOVABLE VALVE ASSEMBLY WITH REMOVABLE SIDE PORT" and insert -- INTRODUCER HAVING A VALVE ASSEMBLY AND REMOVABLE SIDE PORT --, therefor.

Column 9,
Line 18, delete "therin" and insert -- therein --, therefor.
Line 37, delete "membrane" and insert -- member --, therefor.
Line 39, delete "sliding" and insert -- slidably --, therefor.
Line 41, delete "The" and insert -- An --, therefor.
Line 47, after "sheath" insert -- including --.
Line 49, delete "moveable" and insert -- movable --, therefor.
Line 55, insert -- the -- before "sheath".
Line 62, delete "An" and insert -- The --, therefor.
Line 65, delete "claim 13" and insert -- claim 12 --, therefor.

Column 10,
Line 8, after "adapted" insert -- to rotate --.
Line 51, delete "positon" and insert -- position --, therefor.
Line 58, delete "aseembly" and insert -- assembly --, therefor.
Line 61, delete "removalbe" and insert -- removable --, therefor.

Signed and Sealed this

Twenty-ninth Day of June, 2004

JON W. DUDAS
*Acting Director of the United States Patent and Trademark Office*